United States Patent [19]

Plischke

[11] Patent Number: 5,599,336
[45] Date of Patent: Feb. 4, 1997

[54] ABSORBENT HYDROGEL FINES IN ABSORBENT STRUCTURES

[75] Inventor: Manfred Plischke, Steinbach/Ts, Germany

[73] Assignee: The Procter & Gamble Company, Cincinnati, Ohio

[21] Appl. No.: 360,766

[22] PCT Filed: Jun. 22, 1993

[86] PCT No.: PCT/US93/05940

§ 371 Date: Dec. 22, 1994

§ 102(e) Date: Dec. 22, 1994

[87] PCT Pub. No.: WO94/01068

PCT Pub. Date: Jan. 20, 1994

[30] Foreign Application Priority Data

Jul. 2, 1992 [EP] European Pat. Off. .............. 92202008

[51] Int. Cl.⁶ .......................... A61F 13/15; A61F 13/20
[52] U.S. Cl. .................... 604/368; 604/358; 604/367; 604/372; 604/378
[58] Field of Search ................................ 604/358, 368, 604/378, 372, 367

[56] References Cited

U.S. PATENT DOCUMENTS

| | | |
|---|---|---|
| 32,649 | 4/1988 | Brandt et al. . |
| 3,661,875 | 5/1972 | Sieja . |
| 4,076,663 | 2/1978 | Masuda et al. . |
| 4,093,776 | 6/1978 | Aoki et al. . |
| 4,610,678 | 9/1986 | Weisman et al. . |
| 4,625,001 | 11/1986 | Tsubakimoto et al. . |
| 4,655,757 | 4/1987 | McFarland et al. . |
| 4,666,983 | 5/1987 | Tsubakimoto et al. . |
| 4,699,823 | 10/1987 | Kellenberger et al. . |
| 4,734,498 | 3/1988 | Cooper . |
| 4,778,460 | 10/1988 | Braun et al. . |
| 4,822,453 | 4/1989 | Dean et al. . |
| 4,824,901 | 4/1989 | Alexander et al. . |
| 4,834,735 | 5/1989 | Alemany et al. . |
| 4,888,093 | 12/1989 | Dean et al. . |
| 4,889,595 | 12/1989 | Herron et al. . |
| 4,889,596 | 12/1989 | Schoggen et al. . |
| 4,889,597 | 12/1989 | Bourbon et al. . |
| 4,898,642 | 2/1990 | Moore et al. . |
| 4,923,454 | 5/1990 | Seymour et al. ................. 604/368 |
| 4,935,022 | 6/1990 | Lash et al. . |
| 5,047,023 | 9/1991 | Berg . |
| 5,061,259 | 4/1991 | Goldman et al. . |
| 5,064,582 | 11/1991 | Sutton et al. . |
| 5,217,445 | 6/1993 | Young et al. . |
| 5,300,565 | 4/1994 | Berg et al. . |
| 5,304,161 | 4/1994 | Noel et al. ...................... 604/378 |
| 5,350,799 | 9/1994 | Woodrum et al. . |
| 5,384,179 | 1/1995 | Roe et al. . |

FOREIGN PATENT DOCUMENTS

| | | |
|---|---|---|
| 212618 | 3/1987 | European Pat. Off. ......... A61F 13/00 |
| 325416 | 7/1989 | European Pat. Off. ......... A61F 13/18 |
| 339461 | 11/1989 | European Pat. Off. ......... A61F 13/18 |
| 417761 | 3/1991 | European Pat. Off. ......... B29B 17/00 |
| 463388 | 1/1992 | European Pat. Off. ......... C08J 3/12 |
| WO91-15368 | 10/1991 | WIPO . |
| WO92-18171 | 10/1992 | WIPO . |

Primary Examiner—John G. Weiss
Assistant Examiner—Francis K. Cuddihy
Attorney, Agent, or Firm—Edward J. Milbrada; T. David Reed; Steven W. Miller

[57] ABSTRACT

The present invention relates to absorbent structures for disposable absorbent articles containing absorbent hydrogel particles. Particularly, the invention relates to absorbent structures having the absorbent hydrogel particles distributed such that essentially only particles of less than 105 micrometers are distributed in a dusting layer which, in a disposable absorbent article is adjacent the backsheet side of the absorbent article, and particles of 105 micrometers or larger are distributed in a primary layer.

12 Claims, 4 Drawing Sheets

ABSORBENT HYDROGEL FINES IN ABSORBENT STRUCTURES

The present application is a 371 of PCT/US93/05940 filed Jun. 22, 1993.

FIELD OF THE INVENTION

The present invention relates to absorbent structures for disposable absorbent articles containing absorbent hydrogel particles. More particular, the invention relates to absorbent structures having the absorbent hydrogel particles distributed such that essentially only particles of less than 105 micrometers are distributed in a dusting layer, which in a disposable absorbent article is adjacent the backsheet side of the absorbent article, and particles of 105 micrometers or larger are distributed in a primary layer.

BACKGROUND OF THE INVENTION

In the field of absorbent structures for disposable absorbent articles like for example baby diapers, adult incontinence briefs, pads or sanitary napkins it has become common to use absorbent hydrogel material especially in particulate form. A large variety of designs improving the functionality of the absorbent hydrogel particles are known and are for example disclosed in EP-A-212 618, WO-9101163 or EP-A-325 416. More recently it has become known that many of the particulate absorbent hydrogel particles have an appreciable performance profile in respect to particle size. This has led to even further advanced absorbent structures utilizing the previously known amounts of absorbent hydrogel particles but limiting the particle size of the absorbent hydrogel particles to a specific range. Absorbent articles comprising structures of this or similar designs have been disclosed for example in U.S. Pat. No. 5,061,259 pending U.S. patent applications Ser. Nos. 07/684,712, 07/684,374 now U.S. Pat. No. 5,233,443, U.S. Ser. No. 07/684,633, U.S. Ser. No. 07/685,255 all filed on Apr. 12, 1991 or EP-A-339 461.

Since the specific particle size range required in these absorbent articles excludes the smaller particles, referred to as "fines" and defined hereinafter, the problem how to utilize these smaller absorbent hydrogel particles arose. This problem is for example disclosed in EP-A-417 761. Disposal of fines can almost be ruled out as a solution since it can cause an environmental problem and is commercially not attractive. As an alternative, the recycling of fines already during the manufacturing process of absorbent hydrogel particles is suggested in EP-A-463388 and EP-A-417761. However, the large quantities produced and the different production processes used for making absorbent hydrogel particles do not always allow immediate resolution of the problem by modifications of the manufacturing process. Also during transport interparticle friction between absorbent hydrogel particles can lead to fines being generated regardless of the initial particle size. In summary, these considerations suggest to search for alternative ways to utilize fines.

Therefore, it is an objective of the invention to utilize absorbent hydrogel particle fines in absorbent structures without incurring the problems previously resolved by selecting an absorbent hydrogel particle size distribution which omitted fines. It is also an objective of the invention to provide a process which allows to continue to utilize absorbent hydrogel particles of a full particle size distribution range thus eliminating the need for modifications to the manufacture of absorbent hydrogel particles.

In a different aspect of the invention a further improvement of the design of absorbent articles is provided by incorporation of the absorbent structures according to the present invention. A design characteristic of absorbent articles is that the liquid impervious backsheet requires protection from being penetrated by dry absorbent hydrogel particles to maintain liquid imperviousness. Some designs afforded the extra cost of a high basis weight backsheet strong enough to withstand penetration or marking by absorbent hydrogel particles. Other more practical designs included a protective layer of fibrous, often also absorbent, material between backsheet and the absorbent structure which comprises the absorbent hydrogel particles. This had the added advantage of supplying some extra absorbent capacity while protecting the backsheet. Two well known executions of this absorbent article design are either to include a tissue layer or, more preferably, creating an absorbent structure which had the absorbent hydrogel particles only distributed above a thin protective layer, designated dusting layer, of the absorbent structure. However, even this most advanced design including a dusting layer had the disadvantage that part of the absorbent structure was only utilized to a suboptimal extent since the dusting layer by design could not contain absorbent hydrogel particles.

Therefore, a third objective of the invention is to supply absorbent articles having a dusting layer to prevent penetration or marking of the backsheet by absorbent hydrogel material particles in which the absorptive function of the dusting layer is optimized by incorporation of absorbent hydrogel fines.

An additional objective of the present invention is to combine the elimination of problems associated with the utilization of absorbent hydrogel particles in absorbent articles with the improvements in absorptive function by including absorbent hydrogel particles in the dusting layer of absorbent structures.

SUMMARY OF THE INVENTION

In a first aspect the present invention provides absorbent structures for absorbent articles like disposable baby diapers, disposable adult incontinence briefs, pads or sanitary napkins.

In a second aspect the present invention provides absorbent articles which comprise a liquid permeable topsheet, a liquid impermeable backsheet and the absorbent structure according to the first aspect of the present invention which is disposed between the topsheet and the backsheet. According to the invention the absorbent structure comprises two absorbent layers, one layer being designated dusting layer, the other layer being designated primary layer. Within the absorbent structure the dusting layer is the layer which in an absorbent article is adjacent to the backsheet and the primary layer is the layer which in an absorbent article is adjacent to the topsheet. Adjacent as used in this context includes but is not limited to direct contact in a face to face relationship. For example additional layers may be disposed between topsheet and primary layer to further improve absorbent performance of the absorbent article.

Both absorbent layers are formed by a fibrous, matrix in which absorbent hydrogel particles are distributed. The absorbent hydrogel particles distributed in the primary layer are selected to have a particle size distribution such that at least 70% by weight have a particle size of 105 micrometers or larger. The absorbent hydrogel particles distributed in the dusting layer are selected to have a particle size distribution such that at least 60% by weight have a particle size of less than 105 micrometers.

In a preferred execution of the absorbent article of the present invention the dusting layer is in a face to face relationship to the backsheet. Equally preferred, but particularly preferred if the dusting layer has direct contact in a face to face relationship with the backsheet, are absorbent articles in which all absorbent hydrogel particles distributed in the dusting layer have a particle size of less than 105 micrometers.

It is an additional aspect of the present invention to provide a process by which the absorbent structures of the invention can be manufactured. In its process aspect the invention comprises at least the following process steps: first, continuously moving two gas streams which have suspended in each gas stream a, preferably homogeneous, blend of the matrix fibres and the absorbent hydrogel particles in such particle size distribution as to form the dusting layer and the primary layer of the absorbent structure according to the definition of the product invention.

A second process step is continuously laying the laminates blend of matrix fibres and absorbent hydrogel particles of each gas stream down on top of each other onto a continuously moving lay-down means to form a dusting layer and a primary layer. The lay-down means for this process preferably can either be a screen, mounted on a rotating lay-down drum or a translational moving lay-down belt.

In a process utilizing a rotating lay-down drum, it is particularly preferred that the dusting layer is placed closer to the screen of the lay-down drum than the primary layer. If a translational moving lay-down belt is used in the process according to the invention, it is preferred that the primary layer is placed closer to the belt than the dusting layer.

BRIED DESCRIPTION OF THE DRAWINGS

While the specification concludes with claims, particularly pointing out and claiming the present invention it is believed that the present invention will be better understood from the following description in conjunction with the accompanying drawings in which:

DETAILED DESCRIPTION OF THE INVENTION

Figure 1:
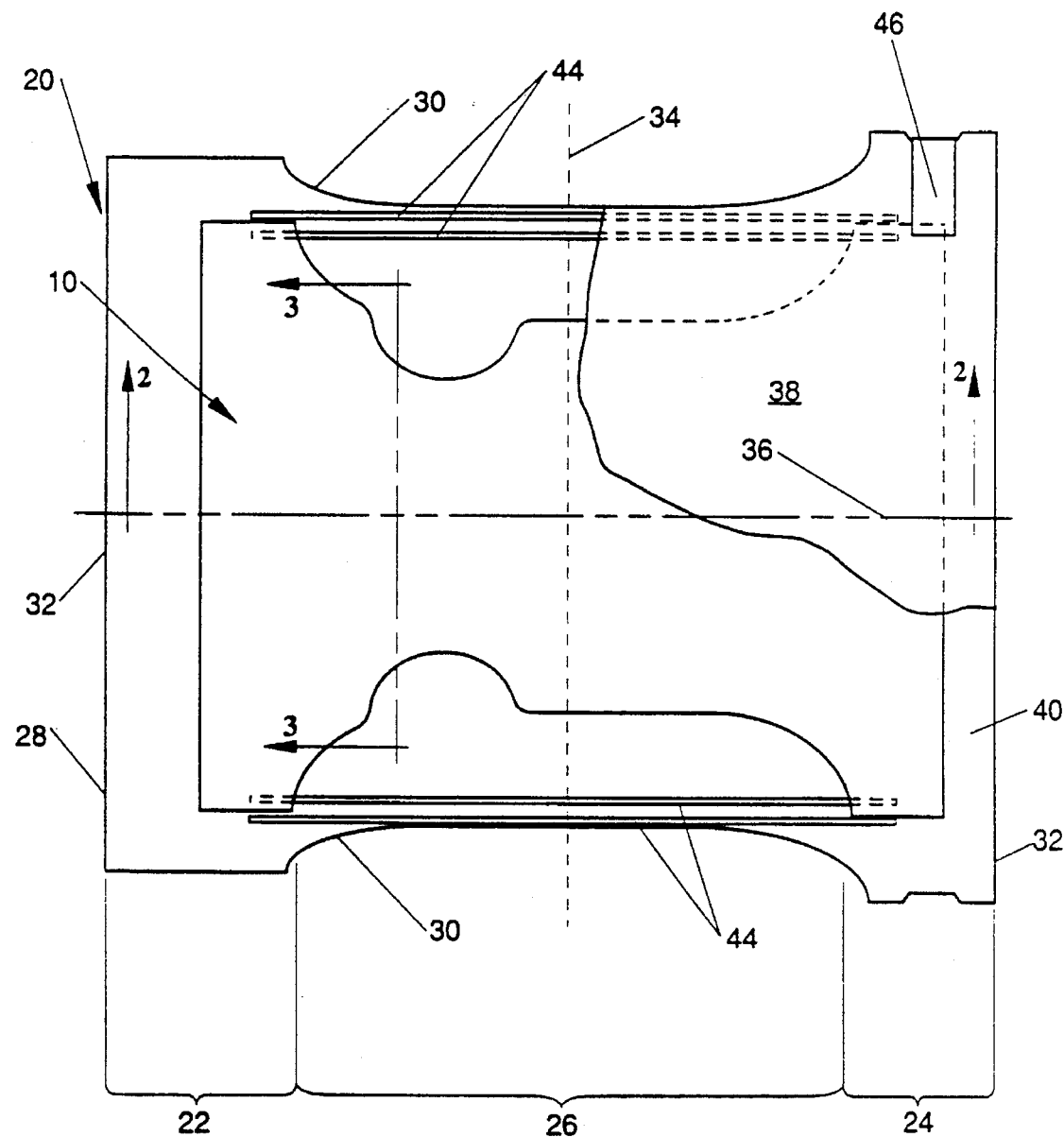
FIG. 1 is a plan-view of a disposable diaper embodiment of the present invention wherein most of the topsheet has been cut away to most clearly show the underlying absorbent core (an embodiment of an absorbent structure of the present invention) of the diaper.

The present invention provides absorbent structures for disposable absorbent articles such as diapers, adult incontinence briefs, pads or sanitary napkins. The absorbent structure of the present invention comprises two distinct layers designated dusting layer and primary layer. Both layers are similar in that they comprise a fibrous matrix in which absorbent hydrogel particles are disposed, preferably in a homogenous way. Both layers are distinguished by the particle size distribution of each layer. The different distribution is such that the absorbent hydrogel particles in the dusting layer together with the absorbent hydrogel particles in the primary layer represent a standard bulk particle size distribution. The term "standard bulk particle size distributions", as used herein, refers to those particle sizes in the range typically received from commercial superabsorbent material suppliers.

In the following a detailed description of the individual materials and components of the absorbent structures as well as of the absorbent articles which utilize the absorbent structure is provided.

A. The Absorbent Structure

The absorbent structures of the present invention will be described herein in relation to their use in absorbent articles; however, it should be understood that the potential application of the absorbent structure should not be limited to the specific absorbent articles described herein.

The absorbent structures of the present invention are capable of absorbing and retaining liquids. These liquids can be, but are not limited to water and certain body exidates. Preferably, when used in absorbent articles of the type described above, the absorbent structures are generally soft, compressable, conformable and non-irritating to the skin.

As said herein above, the absorbent structure comprises a dusting layer and a primary layer which are placed onto each other. The direction defined perependicular to the plane of the dusting layer and the primary layer is hereinafter referred to as Z-direction. The positive Z-direction is from dusting layer towards primary layer, while the negative Z-direction is opposed thereto. When used in absorbent articles, the absorbent structure is placed such that its positive Z-direction points towards the body of the person when the absorbent article is used.

The shape of the absorbent structure in the plane perpendicular to its Z-direction is defined according to its particular use in an absorbent article. In principle, there is no limitation as to which shape the absorbent structure may have. However, for absorbent diapers, incontinence briefs, sanitary pads, catamenials or pantiliners, the most common shapes known and useful in the present invention are rectangular, preferably with rounded edges, hourglass or dogbone shaped, T-shaped, or oval. In general the shapes of absorbent structures are preferred which allow the absorbent article, in which the absorbent structure is used, to best provide comfort, form fitting and absorbent function. For absorbent diapers this would be T-shaped, dogbone or hourglass shapes. Other shapes like circular disks are used for example in brassier inserts or inlays for breast-feeding mothers.

Figure 4:
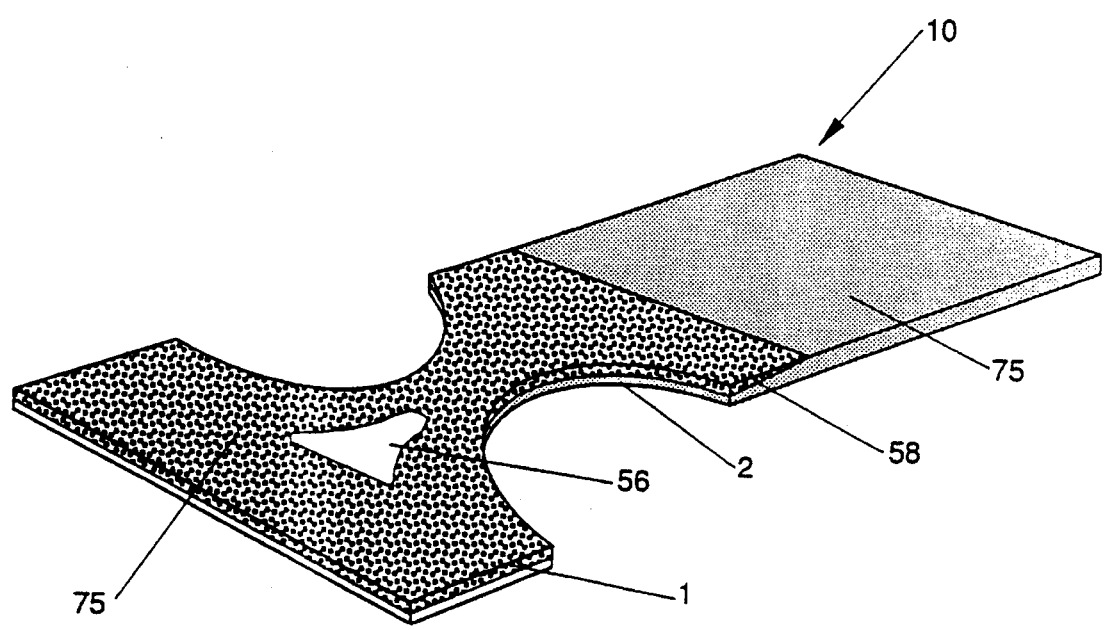
FIG. 4 is a perspective view of another alternative embodiment of an absorbent structure of the present invention

FIG. 1 shows a particular preferred shape of the absorbent structure (10) in the context of a disposable absorbent diaper (20). The absorbent structure (10) of FIG. 1 also has a longitudinal axis (36) and a lateral axis (34) which are perpendicular to each other and both are perpendicular to the Z-direction. It can be seen from FIG. 1 that a preferred shape of the absorbent structure and absorbent article is symmetrical to the longitudinal axis (36) but has a distinct difference between the two longitudinal portions of the absorbent structure. FIG. 4 shows another preferred absorbent structure (10) for disposable absorbent diapers or incontinence briefs. This shape typically is designated T-shape absorbent structure.

The shapes of the individual dusting layer and primary layer of the absorbent structure can be coextensive. However, for many absorbent article applications, the shape of the primary layer and the dusting layer are not coextensive. According to the invention, the dusting layer and the primary layer only need to be placed onto each other in the region of the liquid entry point. For example, this is the region of the urination point in disposable absorbent diapers.

It is particularly preferred that the dusting layer is coextensive with the full shape of the absorbent structure while the primary layer is disposed on the dusting layer and covers only a portion therof. A preferred execution of an absorbent structure for a disposable absorbent diaper has a dusting layer which is coextensive to the shape of the absorbent structure while the primary layer extends fully along the longitudinal axis (36), i.e. from end to end of the absorbent structure while in lateral direction (34) the absorbent structure extends to less than the largest width of the absorbent structure (10), particularly preffered less than the smallest width of the absorbent structure (10). Alternatively as shown in FIG. 4, the primary layer (1) may extend only partially in longitudinal direction (36) of the absorbent structure while being co-extensive with the dusting layer (2) in lateral direction. Most preferred are absorbent structures, in particular for absorbent diapers, which have a primary layer of less than the full longitudinal length of the absorbent structure and a lateral extension of less than the largest lateral extension of the absorbent structure. This will provide most effective, i.e ecological and economical, usage of the absorbent materials which are comprised in the primary layer.

The dusting layer and the primary layer can have variable or uniform basis weight, density and thickness in longitudinal or lateral direction. FIG. 4 shows an absorbent structure (10) having a low density acquisition zone (56) in the primary layer (1). The low density acquistion zone (56) of this embodiment of the invention has a rounded triangular shape and is designed according to U.S. Pat. 4,834,735. Also from FIG. 4, a region of transition (58), where the primary layer (1) ends, can be part of the absorbent structures (10) according to the invention. In such a transition region the basis weight, density or thickness or a combination of these variables changes in the respective layer. In a preferred execution of an absorbent structure for absorbent diapers such a transition region (58) is incorporated into the primary layer (1) where such a primary layer is not coextensive with the dusting layer (2) in longitudinal or lateral direction.

The term "basis weight" as used herein refers to a weight of material which is disposed in an area perpendicular to the Z-direction and divided by the size of the area to which the material corresponds. For example the basis weight can be measured by die-cutting an area of 1.0 or 6.45 square centimeters of the layer or the absorbent structure as a whole and weighing the sample on a standard scale. As indicated above the basis weight depends on the lateral and longitudinal coordinates of a layer or the absorbent structure.

B. The Absorbent Hydrogel Material

The absorbent hydrogel materials used in the present invention are substantially water insoluble, absorbent, polymer materials that are capable of absorbing large quantities of fluid such as water and body exudates in relation to their weight in forming hydrogels in the process. Such materials are usually also capable of retaining such absorbed fluids under moderate pressures. Absorbent hydrogel materials may also be referred to by other names such as simply "superabsorbent materials" or "hydrocolloids" or "absorbent gelling materials". The types of absorbent hydrogel materials useful in the present invention may vary widely.

The absorbent hydrogel materials that are preferred for use in the present invention have an Absorptive Capacity (as measured by the test set forth herein) of at least about 18–20 grams, and more preferable at least about 25 grams, of Synthetic Urine per gram of the absorbent hydrogel material (in its dry state). Typically, the absorbent hydrogel material used in the present invention will have an Absorptive Capacity of from about 30 to about 45 grams of Synthetic Urine per gram of absorbent hydrogel materials. Absorbent hydrogel materials having Absorptive Capacities in this range are especially useful in absorbent structures in absorbent articles since they can hold high amounts of discharged body exudates such as urine under moderate confining pressures that simulate in-use conditions. It is obvious to those skilled in the art of absorbent structures or absorbent articles that absorbent hydrogel particles are evaluated for the final usage by employing the respective relevant liquid. For example for catamenials or pantiliners different liquids than synthetic urine are appropriate. Different liquids however will cause different Absorptive Capacities to be achieved, therefore the above Absorptive Capacities are not to be considered limiting for the use of absorbent hydrogel particles which are designed to be used for liquids other than urine.

Some general types of suitable particulate absorbent hydrogel materials and methods of making the same, useful in the present invention are described in greater detail in U.S. Pat. No. Reissue 32,649 entitled "Hydrogel-Forming Polymer Compositions For Use in Absorbent Structures" reissued to Brandt et al. on Apr. 19, 1988.

The general types of particles suitable for use in the present invention may also be those particles that are referred to as "precursor" particles in the following U.S. Patents U.S. Pat. Nos. 5,384,179 entitled "Particulate Polymeric Compositions Having Interparticle Crosslinked Aggregates of Fine Precursors" filed in the names of Donal Carroll Roe, et al. U.S. Pat. No. 5,124,188 entitled "Porous, Absorbent, Polymeric Macrostructures and Method of Making the Same" filed in the names of Donald Carroll Roe, et al.; Ser. No. 07/503,499 entitled "Method for Producing Polymeric Compositions Containing Interparticle Crosslinked Aggregates" filed in the names of Frank Henry Lahrman, et al.; U.S. Pat. No. 5,180,662 entitled "Absorbent Members Containing Interparticle Crosslinked Aggregates" filed in the names of Charles John Berg, et al.; U.S. Pat. No. 5,149,334 entitled "Absorbent Articles Containing Interparticle Crosslinked Aggregate" filed in the names of Frank Henry Lahrman, et al.; U.S. Pat. No. 5,300,565 entitled "Particulate, Absorbent, Polymeric Compositions Containing Interparticle Crosslinked Aggregates" filed in the names of Charles John Berg, et al., all filed Apr. 2, 1990. These patent applications may be referred to collectively as the "Inter-Particle Crosslinked Aggregate" applications.

The absorbent hydrogel material particles may optionally be surface treated as described in the Inter-Partical Crosslinked Aggregates applications. Thus the absorbent hydrogel material particles may be surface treated as described in U.S. Pat. No. 4,824,901. If surface treated, the absorbent hydrogel material particles are preferably surface treated by applying a surface crosslinking agent onto the particles and reacting the surface crosslinking agent with the polymer material at or near or in the proximity of the surface of the particles.

The absorbent hydrogel materials may also have the level of extractable polymer material specified in U.S. Pat. No. Reissue 32,649.

The preferred polymer materials for use as the absorbent hydrogel material particles possess a carboxyl group. These polymers include hydrolyzed starchacrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolized acrylonitrile or acrylamide copolymers, slightly network crosslinked products of any of the foregoing copolymers, partially neutralized polyacrylic acid. These polymers may be used either independently or in the form of a mixture of two or more monomers, compounds, or the like. Examples of these polymer materials are disclosed in U.S. Pat. Nos. 3,661,875, 4,076,663, 4,093,776, 4,666,983, and 4,734,498.

The most preferred polymer materials for use as the absorbent hydrogel material particles are slightly network crosslinked products of partially neutralized polyacrylic acids and starch derivates therefrom. Most preferably, the particles comprise from about 50% to about 95%, preferably about 75%, neutralized, slightly network crosslinked, polyacrylic acid (e.g., poly (sodium acrylate/acrylic acid)).

The individual particles of polymer material may be formed in any conventional manner. Typical and preferred processes for producing the particles are described in U.S. Pat. Nos. Reissue 32,649, U.S. Pat. Nos. 4,666,983 and 4,625,001.

The preferred methods for forming the particles are those that involve aqueous solution or other solution polymerization methods as opposed to reverse phase polymerization (the latter also being known as "inverse phase polymerization" or "emulsion polymerization"). As described in U.S. Pat. No. Reissue 32,649, aqueous solution polymerization involves the use of an aqueous reaction mixture to carry out polymerization to form the particles.

The absorbent hydrogel materials incorporated into the absorbent structures of the present invention are in a particulate form. The term "particulate" is used herein to mean that the absorbent hydrogel materials are in the form of discrete units denominated "particles". The particles can comprise granules, pulverulents, spheres, aggregates or agglomerates. However, typically, the particles described herein will largely not be agglomerated or aggregated. The particles can have any desired shape such as cubic; polyhedral; spherical; rounded; angular; irregular; or randomly-sized irregular shapes (e.g., pulverulent products of a grinding or pulverizing step).

The size distribution of the particles of absorbent hydrogel materials is of critical importance to the performance of absorbent structures.

In general, large particles of absorbent hydrogel materials swell slowly and decrease the potential fluid uptake rate (that is, the rate at which fluid is taken into the absorbent structure in the z-direction). Small particles (or "fines") tend to swell rapidly, but are easily forced into capillary spaces, decreasing the structure's permeability and dramatically curtailing the rate of fluid distribution throughout the structure. Also, too high concentrations of fine particles can coagulate into a gel mass that acts as a barrier to fluid distribution. These are the phenomena referred to as "gel-blocking".

By using a specific, relatively narrow, particle size distribution in absorbent structures containing absorbent hydrogel material, the above-mentioned fluid processing limitations of both large and fine particles can be significantly reduced or eliminated. While not wishing to be bound by any particular theory, it is believed that the particle size to some extent determines the potential fluid uptake rate of an absorbent article. This appears true because the fluid uptake rate is dependent on the overall surface area per unit mass of the absorbent hydrogel material. The range of particle sizes (or "breadth of the distribution" of the particle size) impacts both the potential fluid uptake rate and the distribution rate of the structure. Ideally, the breadth of distribution of particle sizes should be small.

The present invention relates to the use of the standard bulk particle size distribution such that no elimination of the finer particles is necessary. In general any distribution can be brought into compliance with the desire to not contain too large particles by appropriate processes like for example milling, crushing or similar and well-known particle size reducing processes. However, the amount of fine particles as pointed out before will generally continue to increase during these processes and be undesirable as of a certain concentration. In particular, the primary core layer should not contain absorbent hydrogel particles which are known to cause gel-blocking phenomena. On the other hand, disposal of such fine particles is not desirable for ecological and economical reasons. With the present invention, it now is possible to continue to use the standard bulk particle size distribution resulting from usual manufacturing processes of absorbent hydrogel particles while not sacrificing the benefits known from utilization of a small range of particle size distribution in the absorbent structure.

Accordingly the present invention relates to absorbent hydrogel particles distributed in the primary layer and having a particle size distribution such that at least 70% by weight of the particle size is 105 micrometers or larger. The absorbent hydrogel particles distributed in the dusting layer have a particle size distribution such that at least 60% by weight have a particle size of less than 105 micrometers. A preferred execution of the absorbent article of the present invention is such that all hydrogel particles in the dusting layer have a particle size of less than 105 micrometers.

The distribution in longitudinal, lateral or Z-direction of the absorbent structure of the absorbent hydrogel particles in the primary layer is independent of the distribution in the dusting layer, and vice versa. In particular, the absorbent hydrogel particles may be concentrated or reduced in concentration in different regions of the absorbent structure. In a preferred execution of the present invention, the absorbent hydrogel particles of the primary layer follow a basis weight or concentration increase in lateral direction towards the longitudinal axis of the absorbent structure while in longitudinal direction the absorbent hydrogel particle basis weight or concentration maximum is centered around the designed entry point for liquids to be absorbed. The basis weight or concentration profile of the absorbent hydrogel articles can follow a gradual or a step distribution function. It is also preferred to have a distribution profile of the absorbent hydrogel articles in the dusting layer along the lateral direction with a maximum around the longitudinal axis of the absorbent structure.

Figure 2:
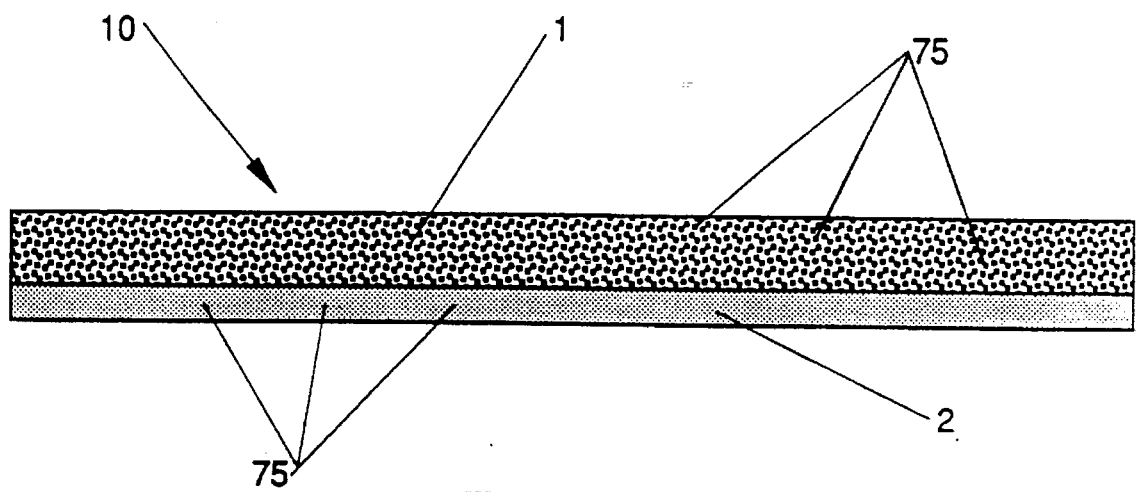
FIG. 2 is a longitudinal sectional view of only the absorbent core of the disposable diaper taken along sectional line 2—2 of FIG. 1.
Figure 3:
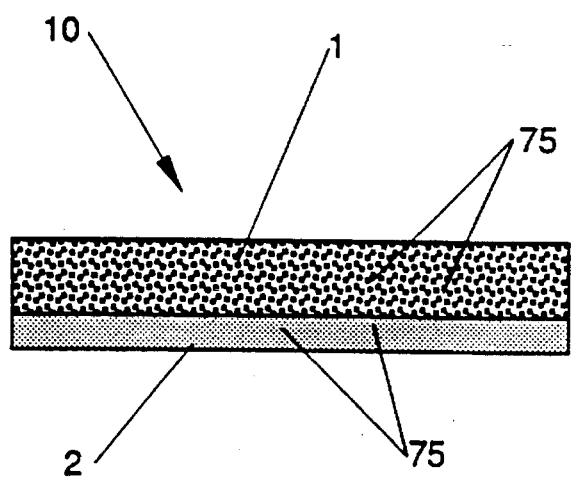
FIG. 3 is a transverse sectional view of only the absorbent core of the disposable diaper taken along sectional line 3—3 of FIG. 1.

Most preferred for the dusting layer as well as the primary layer is an absorbent hydrogel particle distribution in Z-direction which is providing, individually for each layer, a homogeneous profile in Z-direction. This is shown in FIGS. 2 and 3 which show absorbent hydrogel particles (75) homogeneously distributed in the primary layer (1) which have a particle size range of equal to or more than 105 micrometers. The dusting layer (2) of the absorbent structure

(10) also has absorbent hydrogel particles (75) homogeneously distributed in it but they have a particle size of less than 105 micrometers. The cross sections of the absorbent structure (10) of FIG. 1 in longitudinal direction in FIG. 2 and lateral direction in FIG. 3 are not to scale but distorted to provide a better graphical display of the present invention. The concentration itself of absorbent hydrogel particles in Z-direction does not have to be identical for the dusting layer and the primary layer. In fact, it is preferred that the basis weight of the absorbent hydrogel particles in the dusting layer and the basis weight of the absorbent hydrogel particles in the primary layer are in a ratio from 1:1 to 1:20, preferably from 1:2 to 1:5. Basis weights and the indicated ratios have to be present for at least one area, but not throughout the whole area, of an absorbent structure.

The specific size distribution of the absorbent hydrogel material for each layer used in the present invention could be expressed by using the actual dimensions of the particles. A method suitable for determining the actual dimensions of the particles is set forth in greater detail in several of the Inter-Particle Crosslinked Aggregate applications, referred to above. However, determining the actual particle dimensions can be a relatively complicated process due to the different shapes and dimensions that such particles may have. Therefore, for simplicity, the particle sizes in the absorbent structures of the present invention are expressed in another manner.

For purposes of the present invention, the term "particle size" is defined as the dimension of a particle which is determined by a sieve size analysis according to the Sieving Test described in greater detail herein. A sample of particles is sieved as described, and the results are recorded. It should be understood that for particles that are not spherical, the sieving test may determine the size of only certain dimensions of a specific particle. The results of such a sieve size analysis, however, sufficiently define the size of the particles for the purposes of the present invention.

One way to express the size of the particles is in terms of the size of the openings in the sieves. For instance, in principal, a particle that is retained on a sieve with 105 micrometer openings is considered to have a particle size greater than or equal to 105 micrometer for the purposes of the present invention. A particle that passes through a sieve with 297 micrometer openings and is retained on a sieve with 105 micrometer openings is considered to have a particle size from 105 to 297 micrometers. A particle that passes through a sieve with 105 micrometers is considered to have a particle size less than 105 micrometers.

It is well known that in most sieving analyses, certain particles may pass through or be retained on a sieve in one test, and not on another identical test. This can result from the shape of the particle and the different orientation relative to the sieve openings the particle may assume in each test. Because of this, the test results are generally expressed in terms of the percentage of particles, by weight, that will ordinarily pass through a sieve of one dimension and be retained on a sieve of a second dimension. Preferably, in the present invention, no more than about 40%, more preferably no more than about 10%, by weight of the particles should be larger than 105 micrometers for the dusting layer and no more than about 30%, more preferably no more than about 10% by weight of the particles should be smaller than 105 micrometers for the primary layer of the absorbent structure. Particularly preferred for economical reasons is to utilize all particles with 105 micrometers or above from a standard bulk particle size distribution in the primary layer of an absorbent structure. Thus, all particles in the dusting layer have a particle size of less than 105 micrometers.

It is also known as indicated above that particles which are too large provide sub-optimal performance. Therefore, the particle size of particles in the primary layer should not be larger than 500 micrometers, preferably not larger than 297 micrometers.

Figure 5:
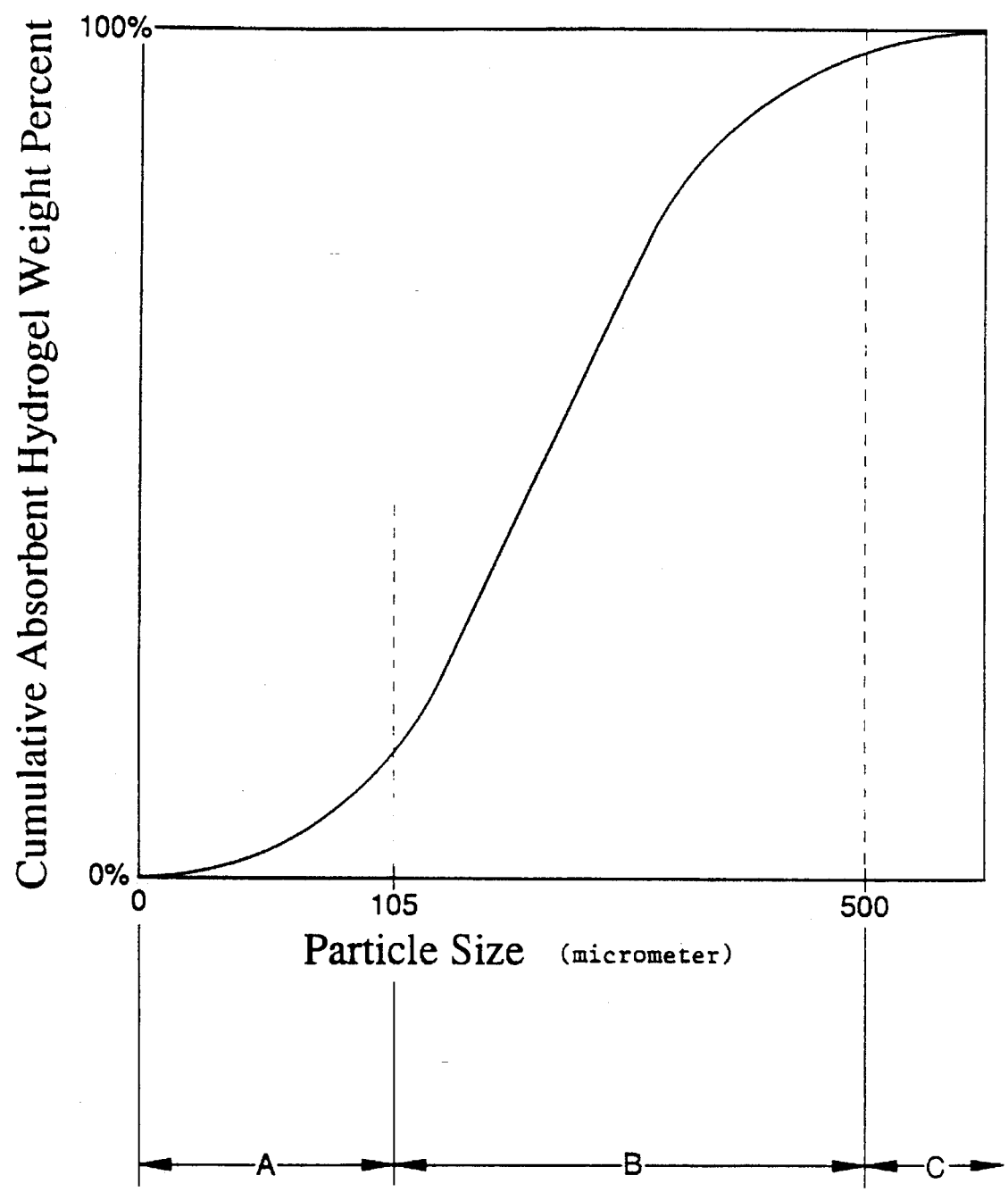
FIG. 5 shows the principal curve of cumulative absorbent hydrogel weight percent versus particle size.

In FIG. 5, the principal curve for a standard bulk particle size distribution integrated to cumulative absorbent hydrogel weight percent versus particle size is shown. The region of the curve designated A would represent the particle size range which according to the invention is put into the dusting layer. The particle size range designated B in FIG. 5 would be incorporated into the primary layer of the absorbent structure according to the invention. Particles which belong to particle size C, that is above 500 micrometers are excluded but can be reduced in size to become part of the particle size range which is fully incorporated into the absorbent structure.

The specific particle size distribution for the dusting layer and for the primary layer described above can be prepared by any suitable method. The specific particle size distribution can be prepared at least in relatively small amounts by a sieving operation. In larger quantities the particle size distributions can be generated for example in cyclone separation processes or other well-known separation processes. Cyclone type separations are preferred since they can be combined with the pneumatic transport system often used for absorbent hydrogel particle handling during the manufacture of absorbent hydrogel particles or even better during the manufacture of the absorbent articles themselves.

C. The Absorbent Matrix

The materials used other than absorbent hydrogel material to form the absorbent structures of the present invention can be in any suitable form provided it is capable of transporting liquids between the structural elements of its matrix. The term "structural elements", as used herein, refers to individual fibers, yarns, strands, loose particles and the like which are typically comprised in absorbent structures of the present invention.

The particles of absorbent hydrogel material are located or dispersed in, or on, the matrix of structural elements. The particles of absorbent hydrogel material are incorporated into the matrix of structural elements forming the dusting layer or the primary layer of an absorbent structure.

Each of the layers of the absorbent structures of the present invention comprises a matrix, such as a web, batt, or other mixture of fiber material with a specific quantity of the particulate absorbent hydrogel material as described herein. Such webs typically comprise entangled masses of fibers also designated fibrous or fiber materials. It should be understood, however, that for the purposes of this invention an absorbent structure is not limited to only comprise a web or the like in the dusting layer and the primary layer. An absorbent structure may also comprise additional laminates, webs, or combinations of several sheets or webs of the types of materials as described herein.

Various types of fiber material can be used in the layers of the absorbent structures of the present invention. Any type of fiber material which is suitable for use in conventional absorbent products is also suitable for use in the absorbent structures described herein. Specific examples of such fiber materials include cellulose fibers, modified cellulose fibers, rayon, polypropylene, and polyester fibers such as polyethylene tereplthalate (DACRON), hydrophilic nylon (HYDROFIL), and the like. Other fiber materials include cellulose acetate, polyvinyl flouride, polyvinylidenechloride, acrylics, polyvinyl acetate, polyamides (such as nylon), bicomponent fibers, tricomponent fibers, mixtures thereof, and the like. Hydrophilic fiber materials, however, are preferred.

The term "hydrophilic", as used herein, describes fibers or surfaces of fibers which are wetted when liquids are deposited onto the fibers. That is, a fiber or its surface is considered to be hydrophilic if water or aqueous body liquids readily spreads on or over the surface of the fiber without regard to whether or not the fiber actually imbibes the fluid or forms a gel. The state of the art respecting wetting of materials defines hydrophilicity (and wetting) in terms of contact angles and the surface tension of the liquids and solids involved. This is discussed in detail in the American Chemical Society Publication entitled *Contact Angle, Wettability, and Adhesion* edited by Robert F. Gould and copyrighted in 1964, which publication is incorporated by reference herein.

Examples of suitable hydrophilic fiber materials, in addition to some already mentioned, are hydrophilized hydrophobic fibers. These include surfactant-treated or silica-treated thermoplastic fibers derived, for example, from polyolefins such as polyethylene or polypropylene, polyacrylics, polyamides, polystryrenes, polyurethanes and the like. In fact, hydrophilized hydrophobic fibers which are in and of themselves not very absorbent and which, therefore, do not provide webs of sufficient absorbent capacity to be useful in conventional absorbent products, may be suitable for use in the absorbent structures of the present invention due to their good wicking properties. This is because the wicking propensity of the fibers is as important, if not more important, than the absorbent capacity of the fiber material itself. This is due to the high rate of fluid uptake and lack of gel blocking properties of the particulate absorbent hydrogel materials used in the absorbent structures of the present invention. In some applications of the present invention, hydrophobic synthetic fibers can also be used but are usually less preferred.

For reasons of availability and cost, cellulose fibers are generally preferred for use as the hydrophilic fiber material of the absorbent structures described herein. Most preferred are wood pulp fibers which are referred to as "airfelt".

Other cellulosic fiber materials which may be useful in some of the absorbent structures described herein are chemically stiffened cellulosic fibers. Preferred chemically stiffened cellulosic fibers are the stiffened, twisted, curled cellulosic fibers which can be produced by internally crosslinking cellulose fibers with a crosslinking agent. The types of stiffened, twisted, curled cellulosic fibers useful as the hydrophilic fiber material of the absorbent structures described herein are described in greater detail in the following patents: U.S. Pat. Nos. 4,822,453, 4,888,093, 4,889,595, 4,889,596, 4,889,597, and 4,898,642.

Especially preferred absorbent structures comprising the dusting layer and the primary layer which both have a structural matrix of airfelt and also both have the absorbent hydrogel particles dispersed homogeneously in Z-direction in the matrix. These absorbent structures are most preferred if they further comprise a layer of chemically stiffened cellulosic fibers on the primary layer on the side opposite the side of the dusting layer to provide an especially rapid acquisitional wicking layer. The layer of chemically stiffened cellulosic fibers may also comprise absorbent hydrogel particles. If present in an execution of the present invention the size of this layer of chemically stiffened cellulosic fibers is preferably substantially free of absorbent hydrogel particles and has a shape of less than the smallest lateral width of the absorbent structure and less than the longitudinal length of the absorbent structure, i.e. it is smaller than the absorbent structure in all directions.

The relative amount of fiber or other suitable type of material and particulate absorbent hydrogel materials used in the absorbent structures of the present invention can be most conveniently expressed in terms of the weight percentage of those components in the absorbent structure. The absorbent structures preferably contain from about 5% to about 98% overall, more preferably from about 10% to about 80%, by weight of the absorbent structure, of the particulate absorbent hydrogel material.

By "overall concentration" in this context is meant the total weight of absorbent hydrogel particles expressed in % of the total weight of the absorbent structure or the respective absorbent layer.

Due to the difference in particle size in the dusting layer and the primary layer the preferred concentration of absorbent hydrogel particles in each layer is not identical. Accordingly, the preferred overall concentration of absorbent hydrogel particles in the dusting layer is from 5% to 50%, most preferably from 10% to 35%, by weight of the dusting layer. On the other hand, it is preferred that the overall concentration of absorbent hydrogel particles in the primary layer is from 10% to 80%, more preferably from 20% to 50%, and most preferably from 30% to 40% by weight of the primary layer.

It is also preferred that the dusting layer and the primary layer have different absorbent capacities. This can be achieved by selecting the overall absorbent hydrogel particle concentration and by using different basis weights for the fibrous matrix in the dusting layer and the primary layer. According to the present invention the ratio of the maximum basis weight of the fibrous matrix in the dusting layer and the maximum basis weight of the fibrous matrix of the primary layer is selected such that it has a range from 1:1 to 1:10, preferably from 1:2 to 1:5 for at least some areas of the absorbent structure. When designing an absorbent structure the ratio can be used to distribute the overall amount of absorbent fibrous matrix material according to the absorbent capacity need for which the absorbent article is designed.

Similarly the basis weight of absorbent hydrogel particles in the dusting layer and the basis weight of absorbent hydrogel particles in the primary layer are advantageously selected, according to the invention, if their ratio falls into the range from 1:1 to 1:20, preferably from 1:2 to 1:5.

The total basis weight of absorbent structures depends on the absorbent article for which the absorbent structure is to be utilized. For the absorbent structures contemplated herein, an advantageous range can be defined which incorporates the differences between the different absorbent structures according to the invention as well as the variation of basis weight of an absorbent structure due to concentration gradients in longitudinal and/or lateral direction. The preferred maximum basis weight for absorbent structures in absorbent articles according to the present invention, is therefore in the range from 0.05 $g/cm^2$ to 0.15 $g/cm^2$.

The density of the absorbent structures described herein can be important in several aspects. It can be important in determining the absorbent properties of the absorbent structures by themselves and the absorbent properties of the articles in which such absorbent structures may be employed. The density of the absorbent structures described herein will generally be in the range from about 0.06 $g/cm^3$ to about 0.5 g/cm$^3$, and more preferably within a range of from about 0.08 g/cm$^3$ to about 0.35 g/cm$^3$. Density values for these structures are calculated from their basis weight and caliper. Caliper is measured under a "gentle" load of 15.9 grams/cm$^2$. The basis weight is measured by die-cutting a certain size sample of the absorbent structure and weighing the sample on a standard scale. The weight and area of the sample determine the basis weight. The density and basis weight values include the weight of the particles of the absorbent hydrogel material.

The absorbent structures of the present invention can contain a variety of optional materials in addition to the fiber or other suitable materials and the absorbent hydrogel materials. Such optional materials can include, for example, fluid distribution aids, anitmicrobials, pH control agents, odour control agents, perfumes, etc. If present, these optional components should generally comprise no more than about 30% by weight of the absorbent structures.

D. Process for Making Absorbent Structures

The preferred fibrous absorbent structures described herein can be prepared by any process or technique that comprises a combination of fibers and particles of absorbent hydrogel material. These absorbent structures are preferably formed by air-laying a substantially dry mixture of fibers and absorbent hydrogel particles and, if desired or necessary, densifying the resulting web. Such a procedure is decribed more fully in U.S. Pat. No. 4,610,678. As indicated in U.S. Pat. No. 4,610,678, the air-laid webs formed by this procedure will preferably comprise substantially unbonded fibers. These webs preferably have a moisture content of 10% or less.

According to the process aspect of the invention a preferred continuous process for the manufacture of absorbent structures according to the invention comprises two steps. First, continuously moving two streams of gas, preferably air. Each of the two streams has suspended in it, preferably homogeneously mixed, the matrix fibers and the absorbent hydrogel particles. One stream has the absorbent hydrogel particle size distribution and the matrix fibers suspended in it which will be comprised in the dusting layer and the other stream has the absorbent hydrogel particle size distribution and the matrix fibers which will be comprised in the primary layer of the absorbent structure suspended in it. The second step of the process is laying the material suspended in its gas stream continuously down onto an also continuously moving lay-down means such that the material form the dusting layer and the primary layer according to the design of the absorbent structure.

Preferably the continuously moving lay-down means can be a screen mounted on a rotating lay-down drum which then is followed by a transfer station where the absorbent structure from the lay-down drum is moved onto a transport means. Another, equally preferred continuously moving lay-down means can be a translational moving screen for example in form of a lay-down belt. No transfer station is required for this lay-down system.

It is especially preferred for the manufacture of disposable absorbent diapers that the dusting layer in case of a rotating lay-down drum, as the continuously moving lay-down means, is placed closer to the screen on the lay-down drum than the primary layer in order to result after the transfer station in an absorbent structure which can be transported on vacuum belts with the dusting layer not being exposed for the majority of its surface to the vacuum belts. This prevents the loss of the absorbent hydrogel particles of small size which are comprised in the dusting layer and could otherwise easily be lost into air-streams created by vacuum belts.

Alternatively, if a translational moving lay-down belt is utilized as the continuous lay-down means, it is advantageous to lay down the primary layer closer to the lay-down belt than the dusting layer, thereby achieving the same situation for further processing as described above for a process using a rotating lay-down drum.

E. The Absorbent Article

The absorbent structures of the present invention are especially suitable for use as absorbent cores in absorbent articles, in particular disposable absorbent articles.

The term "absorbent article", as used herein, refers to articles which absorb and contain body exudates and other fluids. More specifically, the term "absorbent article", as used herein, generally refers to articles which are placed against or in proximity to the body of the wearer to absorb and contain various exudates discharged from the body. The term "disposable absorbent articles", as used herein, are those absorbent articles which are intended to be discarded after a single use. This means the original absorbent article in whole is not intended to be laundered or otherwise restored or reused as an absorbent article, although certain materials or all of the absorbent article material may be recycled, reused, or composted.

A preferred embodiment of an absorbent diaper (20) is shown in FIG. 1. As used herein, the term "diaper" refers to a garment generally worn by infants and incontinent persons about the lower torso of the wearer. It should be understood, however, that the present invention is also applicable to other absorbent articles such as incontinent briefs, incontinent pads, training pants, diaper inserts, sanitary napkins and the like.

FIG. 1 is a plan view of the diaper (20) of the present invention in its flat-out, uncontracted state (i.e., with all the elastic induced contraction removed). Portions of the diaper have been cut-away to more clearly show the construction of the diaper (20). The side of the diaper (20).which contacts the wearer faces the viewer in FIG. 1. Therefore the positive Z-direction defined herein is pointing out towards the viewer of FIG. 1. The diaper (20) is shown in FIG. 1 to have a front waistband region (22), a back waistband region (24), a crotch region (26), and a periphery (28). The periphery (28) is defined by the outer edges of the diaper (20). The longitudinal edges of the diaper (20) are designated (30) and the end edges are designated (32). The diaper (20) additionally has a lateral centerline which is designated (34) and a longitudinal centerline which is designated (36).

The diaper (20) preferably comprises a liquid pervious topsheet (38); a liquid impervious backsheet (40) joined with the topsheet (38) and absorbent structures (10) positioned between the topsheet (38) and the backsheet (40); elastic members (44); and tape tab fasteners (46). The topsheet (38), the backsheet (40), the absorbent structure (10) and the elastic members (44) may be assembled in a variety of well known configurations.

A preferred diaper configuration, however, is described generally in U.S. Pat. No. 3,860,003 entitled "Contractable Side Portions For Disposable Diaper", which issued to Kenneth B. Buell on Jan. 14, 1975. Alternatively preferred configurations for the disposable diapers contemplated herein are described in the following patents: U.S. Pat. No. 4,808,178, entitled "Disposable Absorbent Article Having Elasticized Flaps provided with leakage resistant portions" issued to Mohammed I. Aziz and Ted L. Blaney U.S. Pat. No. 4,695,278 entitled "Absorbent Article Having Dual Cuffs" issued to Michael I. Lawson and U.S. Pat. No. 4,816,025 entitled "Absorbent Article Having a Containment Pocket" issued to John H. Foreman.

FIG. 1 shows a preferred embodiment of the diaper (20) in which the topsheet (38) and the backsheet (40) are coextensive and have length and width dimensions generally larger than those of the absorbent structure (10). The topsheet (38) is associated with and superimposed on the backsheet (40) thereby forming the periphery (28) of the diaper (20).

The front and back waistband regions (22) and (24), respectively of the diaper (20), extend from the end edges (32) of the diaper periphery (28) toward the lateral centerline (34) of the diaper (20). The front and back waistband regions (22) and (24) preferably extend a distance of about 5% of the length of the diaper (20). The waistband regions comprise the upper portions of the diaper (20), which, when worn, encircle the waist of the wearer. The crotch region (26) comprises the portion of the diaper (20) which, when worn, is positioned between the legs of the wearer and covers the lower torso of the wearer. The crotch region (26), thus, defines the area of typical liquid deposition for a diaper (20) or other disposable absorbent article.

The topsheet (38) is compliant, soft feeling, and non-irritating to the wearer's skin. Further, the topsheet (38) is liquid pervious permitting liquids to readily penetrate through its thickness. A suitable topsheet (38) may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet (38) is made of a hydrophobic material to isolate the wearer's skin from liquids in the absorbent structure (10).

A particularly preferred topsheet (38) comprises staple length polypropylene fibers having a denier of about 1.5, such as Hercules type 151 polypropylene marketed by Hercules, Inc. of Wilmington, Del. As used herein, the term "staple length fibers", refers to those fibers having a length of at least about 15.9 mm (0.62 inches).

There are a number of manufacturing techniques which may be used to manufacture the topsheet (38). For example, the topsheet (38) may be woven, nonwoven, spunbound, carded, or the like. A preferred topsheet is carded, and thermally bonded by means well known to those skilled in the fabrics art. Preferably, the topsheet (38) has a weight from about 14to about 25 grams per square meter, a minimum dry tensile strength of at least about 400 grams per centimeter in the machine direction, and a wet tensile strength of at least about 55 grams per centimeter in the cross-machine direction.

The backsheet (40) is impervious to liquids and is preferably manufactured from a thin plastic film, although other flexible liquid impervious materials may also be used. As used herein, the term "flexible" refers to materials which are compliant and which will readily conform to the general shape and contours of the wearer's body. The backsheet (40) prevents the exudates absorbed and contained in the absorbent structure (10) from wetting articles which contact the diaper (20) such as bedsheets and undergarments. Preferably, the backsheet (40) is polyethylene film having a thickness from 0.012 mm to 0.051 mm.

A suitable polyethylene film is manufactured by Monsanto Chemical Corporation and marketed in the trade as Film No. 8020. The backsheet (40) is preferably embossed and/or matte finished to provide a more clothlike appearance. Further, the backsheet (40) may permit vapors to escape from the absorbent structure (10) while still preventing exudates from passing through its thickness.

The size of the backsheet (40) is dictated by the size of the absorbent structure (10) and the exact diaper design selected. In a preferred embodiment, the backsheet (40) has a modified hourglass-shape extending beyond the absorbent core structure (10) a minimum distance of at least about 1.3 centimeters to about 2.5 centimeters around the entire diaper periphery (28).

The topsheet (38) and the backsheet (40) are joined together in any suitable manner. As used herein, the term "joined" encompasses configurations whereby the topsheet (38) is directly joined to the backsheet (40) by affixing the topsheet (38) to intermediate structures which in turn are affixed to the backsheet (40). In a preferred embodiment, the topsheet (38) and the backsheet (40) are affixed directly to each other in the diaper periphery (28) by attachment means such as an adhesive or any other attachment means known in the art. Examples of such attachment means could include a uniform continuous layer of adhesive, a patterned layer of adhesive, or an array of separate lines or spots of adhesive.

The tape tab fasteners (46) are typically applied to the back waistband region (24) of the diaper (20) to provide a fastening means for holding the diaper (20) on the wearer. Only one of the tape tab fasteners is shown in FIG. 1. The tape tab fasteners (46) can be any of those well known in the art, such as the fastening tape disclosed in U.S. Pat. No. 3,848,594 issued to Kenneth B. Buell on Nov. 19, 1974. Tape tab fasteners requiring a designated fastening surface such as highly aggresive adhesive tape tabs or two piece mechanical fasteners, e.g. of the loop/hook kind, can also be used. For these tape tab fasteners the designated fastening system is joined to the diaper (20) at the longitudinally opposed end of the diaper (20).

The elastic members (44) are disposed adjacent the periphery (28) of the diaper (20), preferably along each longitudinal edge (30) so that the elastic members (44) will tend to draw and hold the diaper (20) against the legs of the wearer. Alternatively or additionally, the elastic members (44) may be disposed adjacent either or both of the end edges (32) of the diaper (20) to provide a waistband as well as (or rather than) leg cuffs. For example, a suitable waistband is disclosed in U.S. Pat. No. 4,515,595 entitled "Disposable diapers with elastically contractible waistbands" which issued to David J. Kievit and Thomas F. Osterhage on May 7, 1985. A method and apparatus suitable for manufacturing a disposable diaper having elastically contractible elastic members is described in U.S. Pat. 4,081,301 entitled "Method and apparatus for continuously attaching discrete, stretched elastic strands to predetermined isolated portions of disposable absorbent products".

The elastic members (44) are secured to the diaper (20) in an elastically contractible condition so that in a normally unrestrained configuration, the elastic members (44) effectively contract or gather the diaper (20). The elastic members (44) can be secured in an elastically contractible condition in at least two ways. For instance, the elastic members (44) may be stretched and secured while the diaper (20) may be contracted, such as by pleating, and the elastic members (44) may be secured and connected to the diaper (20) while the elastic members (44) are in their relaxed or unstretched condition.

In the embodiment illustrated in FIG. 1, the elastic members (44) extend essentially the entire length of the crotch region (26) of the diaper (20). The elastic members (44) may, alternatively, extend the entire length of the diaper (20), or any other length suitable to provide an elastically contractible line. The length of the elastic members (44) is dictated by the diaper design.

The elastic members (44) may take a multitude of configurations. The width of the elastic members (44) may, for example, be varied from about 0.25 millimeters to about 25 millimeters or more. The elastic members (44) may comprise a single strand of elastic material or may comprise several parallel or non-parallel strands of elastic material. The elastic members (44) may be rectangular or curvilinear. Still further, the elastic members (44) may be affixed to the diaper in any of several ways which are known in the art. For example, the elastic members (44) may be ultrasonically bonded, heat and pressure sealed into the diaper (20) using a variety of bonding patterns, or simply be glued to the diaper (20).

The absorbent structure (10) of the diaper (20) is positioned between the topsheet (38) and the backsheet (40). The absorbent structure (10) may be manufactured in a wide variety of sizes and shapes (e.g., rectangular, hourglass, asymmetrical, etc.) and from a wide variety of materials. The total absorbent capacity of the absorbent structure (10) should however, be compatible with the design liquid loading for the intended use of the absorbent article or diaper. Further, the size and absorbent capacity of the absorbent structure (10) may vary to accomodate wearers ranging from infants through adults.

A preferred embodiment of the diaper (20) has a modified hourglass-shaped absorbent structure (10). The absorbent structure (10) in a diaper (20) is preferably an absorbent structure (10) according to the preferred embodiments as described herein.

A particularly preferred embodiment of the absorbent structure (10) useful in the present invention is shown in FIG. 4. The principle fibrous matrix of this embodiment described in U.S. Pat. No. 4,834,735 entitled "High Density Absorbent Members Having Lower Density and Lower Basis Weight Acquisition Zone" issued to Miguel Alemany and Charles J. Berg. It discloses absorbent structures having a storage zone and an acquisition zone (56). The storage zone in this disclosure is the pendant of the primary layer (1) of the absorbent structure of the present invention. The acquisition zone (56) has a lower average density and a lower average basis weight per unit area than the rest of the primary layer (1) so that the acquisition zone (56) may effectively and efficiently rapidly acquire discharged liquids.

The primary layer (1) shown in FIG. 4 is preferably made by adding the particulate absorbent hydrogel particles (75) to an air-entrained stream of fibers to affect uniform distribution. On top of a homogeneous dusting layer according to the invention the air-entrained stream of fibers is airlaid into a thickness profiled absorbent structure preform. The thickness profiled absorbent structure preform initially has areas of higher basis weight which define the acquisition zone (56). The absorbent structure preform is calendered preferably to at least a uniform thickness in the liquid deposition region in a fixed-gap calender roll to effect densifying of the absorbent structure (10). This creates a lower average density and a lower average basis weight per unit area acquisition zone (56) relative to that of the primary layer (1).

In an alternative to the embodiments described above, the pore size of the fibers in the absorbent cores may be varied without necessarily varying the density of the fibers to form an acquisition zone (56). For example, fine fiber dimensions of hardwood fluff can be utilized to advantage by substituting at least about 50%, and preferably about 80% to 100%, hardwood fluff fibers for the softwood fibers in the primary layer (1). This can be done because the hardwood fluff has a smaller pore size than the softwood fluff material. As result, a capillarity difference will still be obtained within the scope of this preferred embodiment of the invention, even if the density of each zone is the same. Thus, for example, an absorbent structure (10) can be obtained from using a predominately softwood pulp with a fine pore structure to define the acquisition zone (56) and a predominately hardwood fluff pulp to define the primary layer (1).

In use, the diaper (20) is applied to a wearer by positioning the back waistband region (24) under the wearer's back, and drawing the remainder of the diaper (20) between the wearer's legs so that the front waistband region (22) is positioned across the front of the wearer. The tape-tab fasteners (46) are then secured preferably to outwardly facing areas of the diaper (20).

EXAMPLES

To exemplify the benefit of the present invention, absorbent structures were made according to the following description. The mixture of fibers and absorbent hydrogel particles was homogenius in all cases.

The absorbent matrix material was wood pulp, fiberized from roll fluff pulp, available from Procter & Gamble Cellulose and Specialties Division, Memphis, Tenn., USA. Fiberisation was such as to comply to the design criteria given above for disposable diapers. Total amount of wood pulp in a sample structure was 36, 29 and 23 grams with continuously varying basis weight.

The absorbent hydrogel material used in the examples is Stockhausen SAB produced by Stockhausen GmbH, Krefeld, Germany, in bulk particle size distribution. The particles were separated by sieving into a "Fines" fraction, having a particle size smaller than 105 micrometer and a "Coarse" fraction having a particle size of 105 micrometer or above but smaller than 500 micrometer. The weight ratios of fine to coarse particle size was about 30:70. The total amount of absorbent hydrogel material used in preparing the absorbent structures was 8 and 9 grams. The fine and coarse fractions were used pure when preparing the absorbent structures according to the invention to simulate different weight ratios found in commercial absorbent hydrogel materials. The reference samples were made using unsieved SAB.

For the following table samples were evaluated according to statistical requirements. The samples were taken on the longitudinal center line outside the acquisition zone towards the lateral center line of the absorbent structure.

|  | Example | | |
|---|---|---|---|
|  | I | II | III |
| total amounts of | | | |
| pulp | 36 g | 29 g | 23 g |
| SAB | 8 g | 9 g | 8 g |

| | Composition | | | | | | |
|---|---|---|---|---|---|---|---|
| | A | B | C | D | E | F | G |
| dusting layer | | | | | | | |
| amount SAB | 0 g | 2 g | 0 g | 3 g | 0 g | 2 g | 3 g |
| % SAB of total | 0% | 25% | 0% | 33% | 0% | 25% | 38% |
| concentration of SAB in pulp | 0% | 11% | 0% | 19% | 0% | 16% | 22% |
| primary layer | | | | | | | |
| amount SAB | 8 g | 6 g | 9 g | 6 g | 8 g | 6 g | 5 g |
| % coarse SAB | 70% | 100% | 70% | 100% | 70% | 100% | 100% |
| concentration of SAB in pulp | 29% | 23% | 36% | 27% | 39% | 32% | 28% |

While all the compositions for each example had the same overall material balance, composition B, D, F and G, which are embodiments of the invention, have shown significantly better performance in several laboratory tests against the reference compositions A, C, and E for each respective example I, II and III.

In particular, the demand absorbency and acquisition rate test described below, indicated better performance for all three examples I, II and III when comparing the composition according to the invention with the respective reference.

TEST METHODS

The following procedures are conducted under standard laboratory conditions at 23° C. and 50% relative humidity.

A. Absorptive Capacity

The Absorptive Capacity of the superabsorbent hydrogel-forming material is determined by placing the superabsorbent hydrogel-forming material within a "tea bag", immersing the tea bag in an excess of Synthetic Urine for a specified period of time, and then centrifuging the tea bag for a specific period of time after it is removed from the Synthetic Urine. The ratio of absorbent hydrogel material final weight after centrifuging minus initial weight (net fluid gain) to initial weight determines the Absorptive Capacity.

The tea bag material is cut using a 6 cm×12 cm cutting die, folded in half lengthwise, and sealed along two sides with a T-bar sealer to produce a 6 cm×6 cm square tea bag. The tea bag material utilized is a grade 1234 heat sealable material, obtainable from C. H. Dexter, Division of the Dexter Corp., Windsor Locks, Conn., USA, or equivalent. Lower porosity tea bag material should be used if required to retain fine particles. After the tea bag is constructed, 0.200 grams, plus or minus 0.005 grams, of the absorbent hydrogel material is weighed onto a weighing paper and transferred into the tea bag, and the top (open end) of the tea bag is sealed. An empty tea bag is sealed at the top and is used as a blank. Approximately 300 milliliters of Synthetic Urine are poured into a 1,000 milliliter beaker.

The specific synthetic urine used in the test methods of the present invention is referred to herein as "Synthetic Urine". The Synthetic Urine is commonly known as Jayco SynUrine and is available from Jayco Pharmaceuticals Company of Camp Hill, Pa. The formula for the Synthetic Urine is: 2.0 g/l of KCL; 2.0 g/l of $Na_2SO_4$; 0.85 g/l of $(NH_4) H_2PO_4$; 0.15 g/l $(NH_4)_2 H_2PO_4$; 0.19 g/l of $CaCl_2$ and 0.23 g/l of MgCl2. All of the chemicals are of reagent grade. The pH of the Synthetic Urine is the range of 6.0 to 6.4.

The blank tea bag is submerged in the beaker containing Synthetic Urine. The tea bag containing the absorbent hydrogel material (the sample tea bag) is held horizontally to distribute the material evenly throughout the tea bag. The sample tea bag is then laid on the surface of the Synthetic Urine. The sample tea bag is allowed to wet, for a period of no more than one minute, and then is fully submerged and soaked for 60 minutes.

Approximately two minutes after the first sample is submerged, a second set of tea bags, prepared identically to the first set of blank and sample tea bags, is submerged and soaked for 60 minutes in the same manner as the first set. After the prescribed soak time is elapsed for each set of tea bag samples, the tea bags are promptly removed (using tongs) from the Synthetic Urine. The samples are then centrifuged as described below.

The centrifuge used is a Delux Dynac II Centrifuge, Fisher Model No. 05-100-26, obtainable from Fisher Scientific Co. of Pittsburgh, Pa., or equivalent. The centrifuge should be equipped with a direct read tachometer and an electric brake. The centrifuge is further equipped with a cylindrical insert basket having an approximately 6.35 cm high outer wall with an 21.425 cm outer diameter, a 20.155 cm inside diameter, and 9 rows each of approximately 106 0.238 cm diameter circular holes equally spaced around the circumference of the outer wall, and having a basket floor with six 0.635 cm diameter circular drainage holes equally spaced around the circumference of the basket floor at a distance of 1.27 cm from the interior surface of the outer wall to the center of the drainage holes, or an equivalent. The basket is mounted in the centrifuge so as to rotate, as well as brake, in unison with the centrifuge.

The sample tea bags are positioned in the centrifuge basket with a folded end of the tea bag in the direction of the centrifuge spin to absorb the initial force. The blank tea bags are place to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm. Once the centrifuge has been stabilized at 1,500 rpm, a timer is set for 3 minutes. After 3 minutes, the centrifuge is turned off and the brake is applied.

The first sample tea bag and the first blank tea bag are removed and weighed separately. The procedure is repeated for the second sample tea bag and the second blank tea bag.

The absorptive capacity (ac) for each of the samples is calculated as follows: ac =(sample tea bag weight after centrifuge minus blank tea bag weight after centrifuge minus dry absorbent hydrogel material weight) divided by (dry absorbent hydrogel material weight). The Absorptive Capacity value for use herein is the average absorptive capacity of the two samples.

B. Particle Size Determination by Sieve Analysis ("Sieving Test")

The particle size of the absorbent hydrogel material used in the absorbent structures of the present invention is determined by riffling a representative sample of particles of the absorbent hydrogel material, then passing the sample through a set number of sieves of diminishing screen opening size.

The test procedure is as follows. One hundred grams of a representative sample of the absorben hydrogel material is riffled into between four and eight approximately equal fractions.

One of the fractions is then transferred onto a sieve stack. The sieves used in the test are all US standard sieves. The stack should contain the screen sizes of interest to the experiment. For the analysis of the bulk particle size distribution in following Comparative Examples, the sieve stack contains, from the top, a standard #20 sieve (841 micrometer openings), a standard #30 sieve (595 micrometer openings), a standard #50 sieve (297 micrometer openings), a standard #100 sieve (149 micrometers), a standard #140 sieve (105 micrometer openings), a standard #325 sieve (44 micrometer openings), and a sieve pan.

Alternatively for a more narrow particle size distribution (as well as the particle size distributions set forth in the appended claims), the sieve stack contains, from the top, a standard #50 sieve (297 micrometer openings), a standard #70 sieve (210 micrometer openings), a standard #140 sieve (105 micrometer openings), a standard #170 sieve (88 micrometer openings).

The riffled fraction of the absorbent hydrogel material is sieved with a RO-TAP Testing Sieve Shaker Model SS-5, following the manufacturer's instructions. A RO-TAP sieve shaker is shown in FIG. 21–17 on page 21-19 of the reference publication *Perry's Chemical Engineers' Handbook*, Sixth Edition, McGraw-Hill Book Company, 1984. The RO-TAP sieve shaker holds a series of sieves and rotates and taps the series of sieves with a mechanical motion similar to that used in sieving by hand. The tapping motion is applied by a hammer-like component to a "cork" in the center of the lide which covers the stack of sieves.

The sieve shaker, all sieves, and the sieve pan are obtainable from VWR Scientific of Chicago, Ill. The riffled fraction is shaken for 10 minutes under the follwing conditions. The sieve shaker should deliver between about 140–160 taps/minute. The sieve shaker should oscillate at a rate of approximately 270–300 revolutions per minute. The cork in the center of the sieve shaker lid should protrude exactly 3/16 inch (0.48 cm). The absorbent hydrogel material retained on each sieve and the sieve pan after this process is weighed and recorded.

C. Demand Absorbency Test Method

This method consists of a version of a standard demand wettability test. For reference, standard demand absorbency tests are described in Chatterjee, P. K. (Ed.) Absorbency, Chapter II, pp. 60–62, Elsevier Science Publisher B. V., Amsterdam, The Netherlands (1985).

The apparatus used to conduct this test consists of a square sample basket suspended on a frame. The inside dimensions of the basket are 10.2 cm×10.2 cm. The height of the basket is adjustable via a gear mechanism. A fluid reservoir is placed on an electronic balance directly under the sample basket. The balance is connected to a computer.

There are two different types of sample baskets which may be used, depending on the version of the test being run. The two versions of the test are the "z-direction" version and the x-y plane version. The different versions of the test are used to measure the rate at which a sample of the absorbent core, or other absorbent structure, can absorb fluids that move through the sample in different directions, the "z-direction" and the x-y direction.

The term "z-direction", as used herein, is an orientation with respect to the absorbent article (20) of the present invention if the absorbent article (20) is placed in a Cartesian coordinate system in its flat, laid out condition of FIG. I so that the topsheet (38) of the absorbent article (20) lies in the plane formed by the x and y axes (i.e., horizontal). The longitudinal and lateral centerlines (e.g., 36 and 34) of the absorbent article lie in the x-y plane. The "z-direction" is the direction that is perpendicular to the plane of either surface of the absorbent article (20) when it is in such a flat, laid out configuration.

In the z-direction test, the entire 10.2 cm×10.2 cm bottom of the basket consists of a coarse wire screen. The sample, therefore, contacts the fluid. In this test, the sample is only required to transport the fluid through the thickness of the sample in the vertical, or z-direction. This version of the test provides a measurement of the sample's potential fluid uptake rate.

In the x-y plane test, the wire screen is only present in a 2.54 cm×10.2 cm area along one edge of the sample basket bottom, is made of plexiglas and is fluid impervious. The sides of the sample basket that are in contact with the sample are also made of plexiglas and are fluid impervious (in the x-y plane test, and in the z-direction test). This test requires the sample to first demand the fluid in the z-direction, and then transport it a maximum 7.62 cm in the horizontal (x-y) plane. The results from the x-y plane test provide a measurement of the sample's ability to distribute fluid under potential in-use conditions. Both the z-direction and x-y plane tests are done with the absorbent structure sample confined under a 0.2 psi (138 Pa) load applied evenly to the upper surface of the sample.

The test procedure is as follows. First, a 10.2 cm×10.2 cm sample of an absorbent structure is cut. The fluid reservoir is filled with about 6800 ml of Synthetic Urine and set on an electronic balance under the test apparatus. Then the sample basket is lowered until the fluid level is just at the level near the top of the wire screen. A 10.2 cm×10.2 cm (z-direction) or 2.54 cm×10.2 cm (x-y plane), depending on the test being run, piece of commercially available 2-ply Bounty$^{(R)}$ paper towel is placed on the wire screen in the bottom of the basket. The Bounty$^{(R)}$ towel ensures that consistent fluid contact with the underside of the core sample is maintained throughout the duration of the test.

The applied weight is attached to a square metal plate with dimensions slightly smaller than the inner dimensions of the sample basket. Then the top side of the core sample is attached to the bottom of the above-mentioned plate via double sided tape, or spray adhesive. At time=zero, the sample is placed into the sample basket and the data acquisition programme on the computer is activated. After 30 minutes, the test is stopped and the data analyzed and plotted.

One measurement of importance in analysing the data is the sample's Synthetic Urine Capacity at 30 minutes. Other important properties of the sample are its fluid uptake and distribution rates. The time it takes the sample to reach 90% of its 30 minute capacity provides a simple measure of the average fluid demand rate of the absorbent structure being tested. This is referred to as the t90 time and has units of seconds. A t90 time value can be measured using both the z-direction test and the x-y plane test.

D. Acquisition Rate Test Method

This method evaluates the amount of time it takes for a sample absorbent structure to acquire a certain amount of synthetic urine (as described above). The apparatus used is a cylinder having a closing velve and an opening at the bottom allowing liquid to exit the cylinder over an area of 5 $cm^2$. The cylinder is placed on the absorbent structure with its opening and an amount of 50 ml or 200 ml of synthetic urine is filled into the cylinder to measure the acquisition rate for small or large loadings respectively. When opening the velve the synthetic urine is allowed to freely contact the absorbent structure over the area of 5 $cm^2$ under its own hydrostatic pressure head and is absorbed by the absorbent structure.

The time from first contact of the synthetic urine to the absorbent structure until final absorption of the whole amount is measured and used to determine a theoretical acquisition flow rate for the respective amount of synthetic urine. The timing can also be controlled by electronic sensors connected to a stop-watch like for example electrical resistance switches. The location of measurement on the absorbent structure as well as the inclusion of any additional layer (for example top sheet) between the cylinder and the absorbent structure are taken into account. When comparing absorbent structures by using identical location and layer for all samples to be analysed. Results from the acquisitions rate test method show that essentially be used for comparison between absorbent structure samples. The higher the acquisition rate is, the better the performance of the respective sample.

What is claimed is:

1. An absorbent structure comprising:
    an absorbent dusting layer, said absorbent dusting layer comprising a fibrous matrix in which absorbent hydrogel particles are distributed, wherein at least about 60% of said absorbent hydrogel particles in said dusting layer have a particular size less than 105 micrometers; and
    an absorbent primary layer disposed on said dusting layer, said absorbent primary layer comprising a fibrous matrix in which absorbent hydrogel particles are distributed, wherein at least about 70% by weight of said absorbent hydrogel particles in said primary layer have a particle size of 105 micrometers or larger.

2. A disposable absorbent article comprising:
    a liquid permeable topsheet;
    a liquid impermeable backsheet;
    an absorbent structure disposed between said topsheet and said backsheet, said absorbent structure comprising
        an absorbent dusting layer comprising a fibrous matrix in which absorbent hydrogel particles are distributed, wherein at least about 60% of said absorbent hydrogel particles in said dusting layer have a particle size less than 105 micrometers; and
        an absorbent primary layer disposed on said dusting layer, said absorbent primary layer comprising a fibrous matrix in which absorbent hydrogel particles are distributed, wherein at least about 70% by weight of said absorbent hydrogel particles in said primary layer have a particle size of 105 micrometers or larger.

3. An absorbent article according to claim 2, wherein said particle size of all of said absorbent hydrogel particles in said dusting layer is less than 105 micrometers.

4. An absorbent article according to claim 2 having a Z-direction perpendicular to its longitudinal direction and perpendicular to its lateral direction, wherein said absorbent hydrogel particles in each of said layers are homogeneously distributed in said Z-direction of said absorbent article.

5. An absorbent article according to claim 2, wherein the ratio of the basis weight of said fibrous matrix in said dusting layer to the basis weight of said fibrous matrix in said primary layer is from 1:1 to 1:10.

6. An absorbent article according to claim 2 wherein the ratio of the basis weight of said absorbent hydrogel particles in said dusting layer to the basis weight of said absorbent hydrogel particles in said primary layer is from 1:1 to 1:20.

7. An absorbent article according to claim 2, wherein the maximum basis weight of said absorbent structure is in the range from 0.05 $g/cm^2$ to 0.15 $g/cm^2$.

8. An absorbent article according to claim 2, wherein the overall concentration of said absorbent hydrogel particles in said dusting layer is from 5% to 50% by weight of said dusting layer.

9. An absorbent article according to claim 2, wherein the overall concentration of said absorbent hydrogel particles in said primary layer is from 10% to 80% by weight of said primary layer.

10. An absorbent article according to claim 2, wherein said fibrous absorbent matrix of any of said layers is made of fibers selected from cellulose material, chemically stiffened cellulose material or mixtures thereof.

11. An absorbent article according to claim 2, wherein said absorbent hydrogel particles are made of polyacrylates.

12. An absorbent article according to claim 2, wherein said absorbent article further comprises an acquisitional wicking disposed between said topsheet and said primary layer, at least a portion of said acquisitional wicking layer comprising chemically stiffened cellulose fibers.

* * * * *